United States Patent
Hirota et al.

(10) Patent No.: US 10,555,660 B2
(45) Date of Patent: Feb. 11, 2020

(54) IMAGE PROCESSING APPARATUS, IMAGE PROCESSING METHOD, AND IMAGE PROCESSING PROGRAM

(71) Applicant: OLYMPUS CORPORATION, Tokyo (JP)

(72) Inventors: Masashi Hirota, Hachioji (JP); Tetsuo Nonami, Hino (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 15/651,397

(22) Filed: Jul. 17, 2017

(65) Prior Publication Data
US 2017/0311774 A1    Nov. 2, 2017

Related U.S. Application Data

(63) Continuation of application No. PCT/JP2015/051835, filed on Jan. 23, 2015.

(51) Int. Cl.
*A61B 1/00* (2006.01)
*A61B 1/04* (2006.01)
*A61B 5/00* (2006.01)
*A61B 5/02* (2006.01)

(52) U.S. Cl.
CPC ........ *A61B 1/00009* (2013.01); *A61B 1/0005* (2013.01); *A61B 1/04* (2013.01); *A61B 5/0084* (2013.01); *A61B 5/02007* (2013.01)

(58) Field of Classification Search
CPC ..... A61B 1/00009; A61B 1/04; A61B 1/0005; A61B 5/02007; A61B 5/0084
See application file for complete search history.

(56) References Cited

U.S. PATENT DOCUMENTS

| | | | |
|---|---|---|---|
| 8,303,494 | B2 | 11/2012 | Minetoma |
| 2009/0149706 | A1 | 6/2009 | Yamazaki et al. |
| 2011/0112361 | A1 | 5/2011 | Minetoma |
| 2011/0112362 | A1 | 5/2011 | Minetoma |

(Continued)

FOREIGN PATENT DOCUMENTS

| | | |
|---|---|---|
| JP | 2005-198794 A | 7/2005 |
| JP | 2008-043604 A | 2/2008 |
| JP | 2010-082141 A | 4/2010 |

(Continued)

OTHER PUBLICATIONS

Japanese Office Action dated Jun. 26, 2018 in Japanese Patent Application No. 2016-570448.

(Continued)

*Primary Examiner* — Timothy J Neal
(74) *Attorney, Agent, or Firm* — Scully, Scott, Murphy & Presser, P.C.

(57) ABSTRACT

An image processing apparatus includes: a narrowband image acquisition unit configured to acquire a narrowband image showing inside of a lumen; a white light image acquisition unit configured to acquire a white light image showing the inside of the lumen; and a composite image generation unit configured to combine information of the narrowband image to the white light image, according to a depth of a submucosal object, to generate a composite image for display.

7 Claims, 3 Drawing Sheets

(56) References Cited

U.S. PATENT DOCUMENTS

2012/0154566 A1\* 6/2012 Kaku .................. G02B 23/26
  348/68
2012/0176486 A1\* 7/2012 Maeda ............... A61B 1/00009
  348/68

FOREIGN PATENT DOCUMENTS

| JP | 2011-098088 A | 5/2011 |
| JP | 2012-125461 A | 7/2012 |
| JP | 2012-152413 A | 8/2012 |
| JP | 2013-150712 A | 8/2013 |
| JP | 2014-050594 A | 3/2014 |
| JP | 2014-064778 A | 4/2014 |

OTHER PUBLICATIONS

International Search Report dated Apr. 21, 2015 issued in PCT/JP2015/051835.
Chinese Office Action dated Jul. 4, 2018 in Chinese Patent Application No. 201580073907.3.

\* cited by examiner

IMAGE PROCESSING APPARATUS, IMAGE PROCESSING METHOD, AND IMAGE PROCESSING PROGRAM

CROSS-REFERENCE TO RELATED APPLICATIONS

This application is a continuation of PCT international application Ser. No. PCT/JP2015/051835 filed on Jan. 23, 2015 which designates the United States, incorporated herein by reference.

BACKGROUND

1. Field

The present disclosure relates to an image processing apparatus, an image processing method, and an image processing program which perform image processing on an image.

2. Description of the Related Art

Narrowband light has different absorption and scattering characteristics according to a wavelength, and a narrowband image shows a superficial capillary vessel or the like in mucous membrane at a short wavelength, and the narrowband image shows a deep blood vessel or the like under mucous membrane at a long wavelength. These blood vessels have a structure hardly showed in a white light image, and thus, an image having characteristics of both of the narrowband image and the white light image enables further detailed observation. Against such background, for enabling observation using the characteristics of both the narrowband image and the white light image, a technology is known wherein a result of specific processing performed on an image captured in narrowband light is applied to an image captured in white light to generate an image having the characteristics of both images (e.g., see JP 2012-125461 A).

There is a need for an image processing apparatus, an image processing method, and an image processing program which may generate an image having characteristics of white light images and a narrowband image, and may apply narrowband image information without changing original view of a structure showed in the white light image.

SUMMARY

An image processing apparatus according to the one aspect of the present disclosure includes: a narrowband image acquisition unit configured to acquire a narrowband image showing inside of a lumen; a white light image acquisition unit configured to acquire a white light image showing the inside of the lumen; and a composite image generation unit configured to combine information of the narrowband image to a white light image, according to a depth of a submucosal object, to generate a composite image for display.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present disclosure (hereinafter, referred to as "embodiment") will be described below.

First Embodiment

Figure 1:
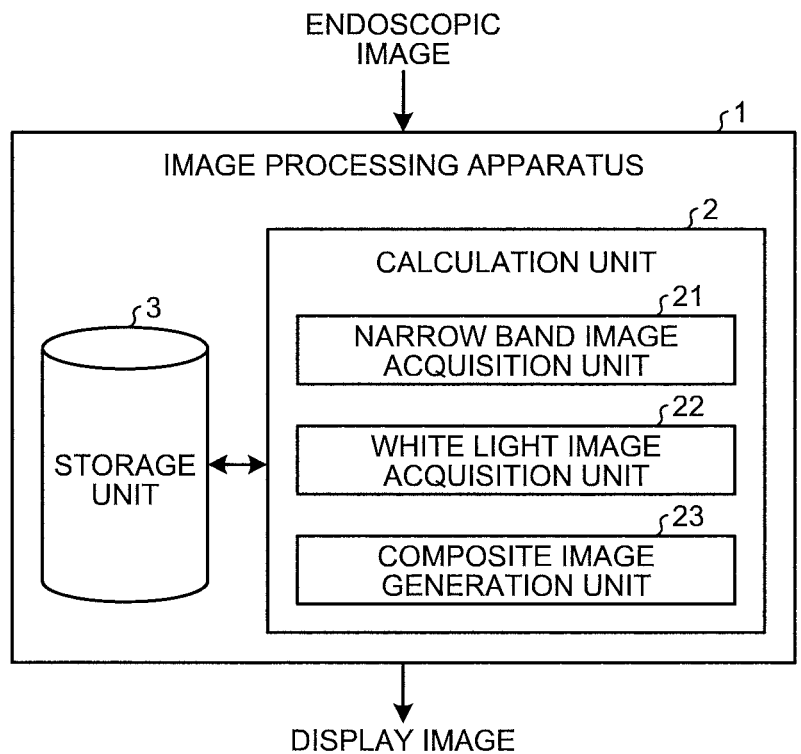
FIG. 1 is a block diagram illustrating a functional configuration of an image processing apparatus according to a first embodiment of the present disclosure.

FIG. 1 is a block diagram illustrating a functional configuration of an image processing apparatus according to a first embodiment of the present disclosure. An image processing apparatus 1 illustrated in FIG. 1 includes a calculation unit 2, and a storage unit 3.

The calculation unit 2 includes a narrowband image acquisition unit 21 configured to acquire a plurality of narrowband images, a white light image acquisition unit 22 configured to acquire a white light image, and a composite image generation unit 23 configured to combine narrowband image information to the white light image to generate a composite image for display.

The narrowband image acquisition unit 21 acquires for example a narrowband image of a center wavelength of $\lambda$ (nm). For adding information about a superficial capillary vessel in mucous membrane to the white light image, a narrowband image of a center wavelength of approximately 415 (nm) is preferably applied. Note that, in this case, the value of the center wavelength is not limited to 415 (nm), and a value in the vicinity thereof may be employed. As a matter of course, the present first embodiment may be also applied to an object, other than the blood vessels, under mucous membrane. Hereinafter, a narrowband image of a center wavelength of $\lambda$ (nm) is represented by an $[\lambda]$ image.

For example, the narrowband image acquisition unit 21 emits narrowband light from a light emitting diode (LED) to the inside of a biological lumen to acquire the narrowband image. Note that, acquisition of the narrowband image is not limited to the above, and for example, the narrowband image may be acquired by performing spectral estimation on the white light image.

The white light image acquisition unit 22 acquires, as the white light image, an intraluminal image captured using a white light source by an endoscope introduced into a living body for observation inside the living body. This white light image is a color image having pixel values corresponding to R (red), G (green), B (blue) wavelength components at each pixel position. Note that, the endoscope mentioned here may employ a fiber endoscope or a capsule endoscope.

The composite image generation unit 23 combines narrowband image information to a white light image to generate a composite image for display. For example, when a [415] image is applied, the composite image generation unit 23 calculates a B component according to the following formula (1).

$$B = w(415, depth) \cdot I([415]) + (1 - w(415, depth)) \cdot baseB \quad (1)$$

Here, on the right side of formula (1), "w(415,depth)" represents a weight at a center wavelength of 415 (nm), at a depth of a submucosal object "depth", "I([415])" represents an intensity of the [415] image intensity, and "baseB" represents the B component of the white light image. The depth "depth" may be obtained by for example applying identification by a classifier generated beforehand using machine learning. Note that the combining is not limited to formula (1). For example, "I([415])" may be combined to a G component. Furthermore, instead of the simple combining "I([415])", frequency information thereof may be combined. When the frequency information is combined, the B component may be calculated according to the following formula (2), for example with a frequency component extracted from the [415] image as "Freq([415])".

$$B = w(415, depth) \cdot Freq([415]) + baseB \quad (2)$$

The weight "w(415,depth)" is defined as a function in which the weight is larger with reducing (shallower) depth "depth" of a submucosal object. Information about a weight "w(λ, depth)" is preferably stored in the storage unit 3 to be referred to upon generation of a composite image by the composite image generation unit 23.

When the [415] image is applied as the narrowband image, the composite image generation unit 23 uses an R component and a G component of the white light image obtained by the white light image acquisition unit 22, in addition to the B component calculated using formula (1), and generates a composite image for display, and outputs the composite image as a display image.

The calculation unit 2 includes a central processing unit (CPU) or hardware such as various arithmetic circuits, reads various programs stored in the storage unit 3 for example to transfer instructions or data to respective units of the image processing apparatus 1, and integrally controls the operation of the image processing apparatus 1 as a whole.

The storage unit 3 stores the information about a weight "w(λ, depth)" described above. Furthermore, the storage unit 3 stores a program operating the image processing apparatus 1, and causing the image processing apparatus 1 to perform various functions, data used during execution of the program, and the like, in addition to image data of the intraluminal image acquired by the image processing apparatus 1. Specifically, the storage unit 3 stores an image processing program according to the present embodiment, and various parameters such as thresholds used in the image processing.

The storage unit 3 is achieved by various IC memories such as a read only memory (ROM) or a random access memory (RAM), a hard disk built in or connected by a data communication terminal, or an information recording device such as a CD-ROM and a reader therefor or the like.

The various programs such as the image processing program stored by the storage unit 3 may be recorded in a computer-readable recording medium. Furthermore, the various programs may be recorded into the storage unit 3 or the recording medium, upon shipping a computer or recording medium product, or may be downloaded via a communication network. Here, the communication network includes for example an existing wired or wireless public switched telephone network, local area network (LAN), or wide area network (WAN).

The image processing apparatus 1 having the configuration described above may be achieved by a single computer, or may be achieved by a plurality of computers. When the image processing apparatus 1 is achieved by the plurality of computers, the computers may perform processing in cooperation with each other, while performing data transmission/reception through the communication network. Note that, here, the computer may include a general-purpose personal computer, a server, or the like.

Figure 2:
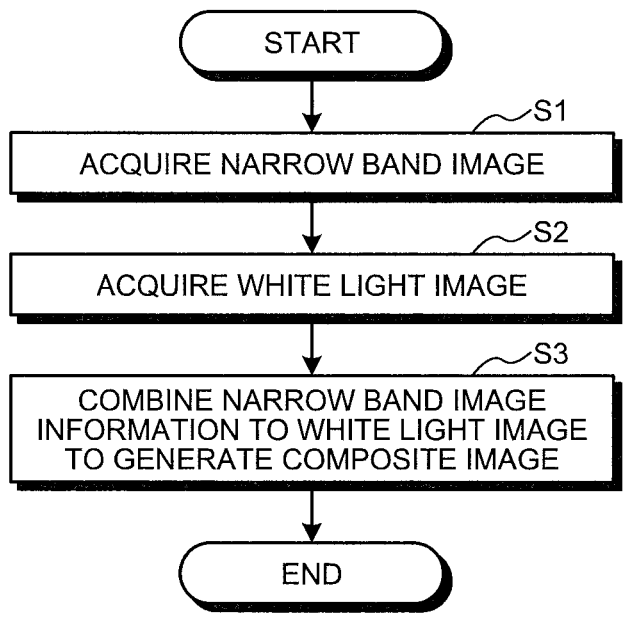
FIG. 2 is a flowchart illustrating the outline of a process performed by the image processing apparatus according to the first embodiment of the present disclosure.

FIG. 2 is a flowchart illustrating the outline of a process performed by the image processing apparatus 1. First, the narrowband image acquisition unit 21 acquires a narrowband image (step S1). The narrowband image acquisition unit 21 acquires for example the [415] image described above.

Next, the white light image acquisition unit 22 acquires a white light image (step S2). The white light image acquisition unit 22 acquires, as the white light image, for example the intraluminal image captured by the endoscope using the white light source.

Then, the composite image generation unit 23 combines narrowband image information to the white light image to generate a composite image for display (step S3). For example, when the [415] image is employed, the composite image generation unit 23 acquires information about the depth "depth" by the classifier generated beforehand using the machine learning, calculates a B component according to the information about the depth "depth", and information about the weight "w(415,depth)" (see formula (1)) stored in the storage unit 3, and uses the B component, and an R component and a G component of the white light image to generate a composite image.

According to the first embodiment of the present disclosure, the narrowband image information may be combined to the white light image, according to the depth of a submucosal object, to generate the composite image for display, so that an image having the characteristics of the white light image and the narrowband image may be generated, and the narrowband image information may be applied without changing the original view of a structure showed in the white light image.

Furthermore, according to the present first embodiment, the depth identification may be used to control the combining of the narrowband image and the white light image, and thus the change in view of the structure showed in the white light image may be prevented, and an image more suitable for observation may be provided.

Note that in the present first embodiment, an arbitrary number of narrowband images may be combined. For example, in addition to the [415] image described above, a narrowband image of a center wavelength of 600 (nm) ([600] image) may be further used to generate a composite image for display. The [600] image includes information about a deep large blood vessel under mucous membrane. In this case, the composite image generation unit 23 calculates an R component according to the following formula (3).

$$R = w(600, depth) \cdot I([600]) + (1 - w(600, depth)) \cdot baseR \quad (3)$$

On the right side of formula (3), a weight w(600,depth) represents a weight at a center wavelength of 600 (nm), at a depth of a submucosal object "depth", and is a function different from that of the weight "w(415,depth)" in formula (1) as a function of the depth "depth". Specifically, the weight w(600,depth) is defined as a function in which the weight is larger with increasing (deeper) depth "depth". In this case, the composite image generation unit 23 uses the G component of the white light image acquired by the white light image acquisition unit 22, in addition to the B component and the R component calculated according to formulas (1) and (3), to generate a composite image. Note that, in this case, the combining is not limited to formulas (1) and (3).

Second Embodiment

Figure 3:
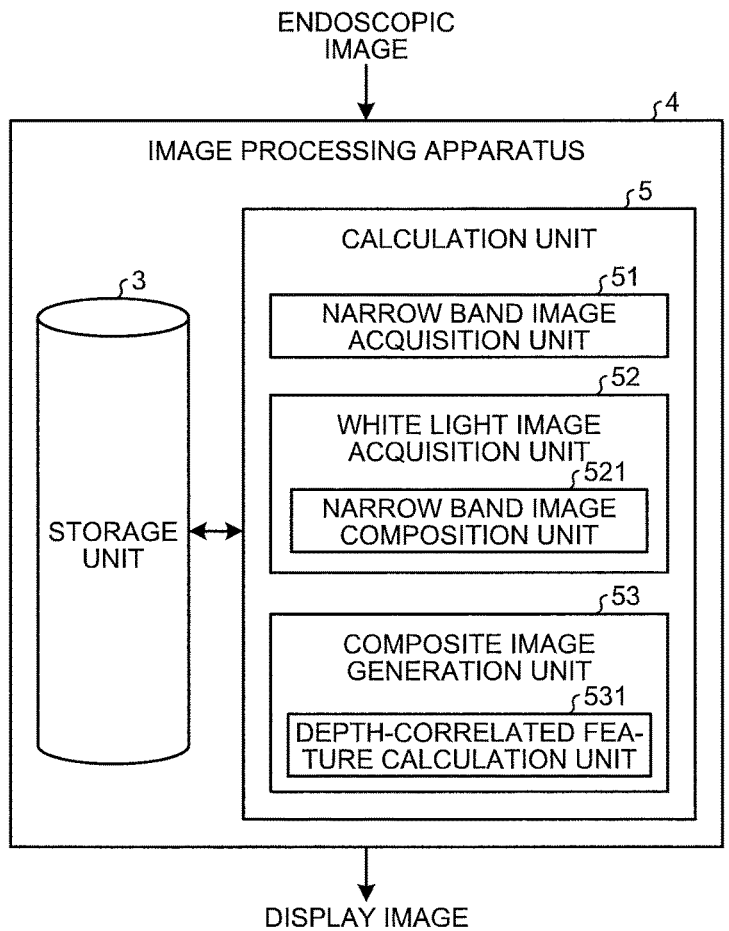
FIG. 3 is a block diagram illustrating a functional configuration of an image processing apparatus according to a second embodiment of the present disclosure.

FIG. 3 is a block diagram illustrating a functional configuration of an image processing apparatus according to a second embodiment of the present disclosure. An image processing apparatus 4 illustrated in FIG. 3 includes a calculation unit 5 and the storage unit 3. Hereinafter, component portions similar to the component portions of the calculation unit 2 of the image processing apparatus 1 according to the first embodiment are denoted by the same reference signs for description.

The calculation unit 5 includes a narrowband image acquisition unit 51 configured to acquire a plurality of narrowband images, a white light image acquisition unit 52 configured to acquire a white light image on the basis of the plurality of narrowband images, and a composite image generation unit 53 configured to combine narrowband image information to the white light image to generate a composite image for display.

The narrowband image acquisition unit 51 acquires, as the plurality of narrowband images, five narrowband images of a [415] image, a [460] image, a [540] image, a [600] image, and a [630] image respectively at a center wavelength of 415 nm, 460 nm, 540 nm, 600 nm, and 630 nm. For example, the narrowband image acquisition unit 21 sequentially emits narrowband light from each LED to the inside of a biological lumen to acquire each of the narrowband images. Note that the center wavelengths of the five narrowband images may be also set to values in the vicinity of the five center wavelengths described above, respectively.

The white light image acquisition unit 52 includes a narrowband image composition unit 521 configured to combine narrowband images corresponding to R, G, and B bands to generate an image corresponding to the white light image. Specifically, the narrowband image composition unit 521 calculates a weighted average of intensities of the [415] image and the [460] image to define a B component of the white light image. Furthermore, the narrowband image composition unit 521 calculates a weighted average of intensities of the [600] image and the [630] image to define an R component of the white light image. Furthermore, the narrowband image composition unit 521 defines intensity of the [540] image as a G component. A weight of a weighted average is preferably set to match a spectral intensity of a wavelength band corresponding to narrowband light in the white light, on the basis of each emission intensity of the narrowband light.

The composite image generation unit 53 includes a depth-correlated feature calculation unit 531 configured to calculate a ratio between the intensities of narrowband images (relative intensity) as a feature correlated to the depth. Specifically, the depth-correlated feature calculation unit 531 calculates a ratio "I([540])/I([415])" between intensities in the [415] image and the [540] image, and a ratio "I([540])/I([600])" between intensities in the [540] image and the [600] image, for each pixel. When the superficial capillary vessel is in an image, the [415] image shows a strong change in absorption, and the intensity of the [415] image is reduced in the corresponding area. In contrast, when a blood vessel in an intermediate layer is in the image, both of the [415] image and the [540] image show a change in absorption, and the intensities of both images are reduced in the corresponding area. Thus, when a blood vessel in a surface layer is in the image, a value of "I([540])/I([415])" tends to be increased relative to that of the blood vessel in the intermediate layer. Similarly, when a blood vessel in a deep layer is in the image, a value of "I([540])/I([600])" tends to be increased relative to that of the blood vessel in the intermediate layer. Accordingly, these ratios may be regarded as the feature correlated to the depth.

The composite image generation unit 53 generates a composite image, on the basis of the features calculated by the depth-correlated feature calculation unit 531. The composite image generation unit 53 determines the B component and the R component respectively combined using the following formulas (4) and (5).

$$B = w\left(\frac{I([540])}{I([415])}\right) \cdot I([415]) + \left(1 - w\left(\frac{I([540])}{I([415])}\right)\right) \cdot baseB \quad (4)$$

$$R = w\left(\frac{I([540])}{I([600])}\right) \cdot I([600]) + \left(1 - w\left(\frac{I([540])}{I([600])}\right)\right) \cdot baseR \quad (5)$$

On the right sides of formulas (4) and (5), a weight $w(x)$ represents a magnitude set according to a ratio x between two narrowband light intensities, and has a value larger with increasing ratio x. In the present second embodiment, the weight $w(x)$ is also stored in the storage unit 3. Note that the [415] image and the [600] image may have weights individually set.

As described above, in the present second embodiment, change of the ratio x between two narrowband light intensities according to the depth of a submucosal object is used to control the combining, and information hardly showed in the white light image is selected to be combined.

Figure 4:
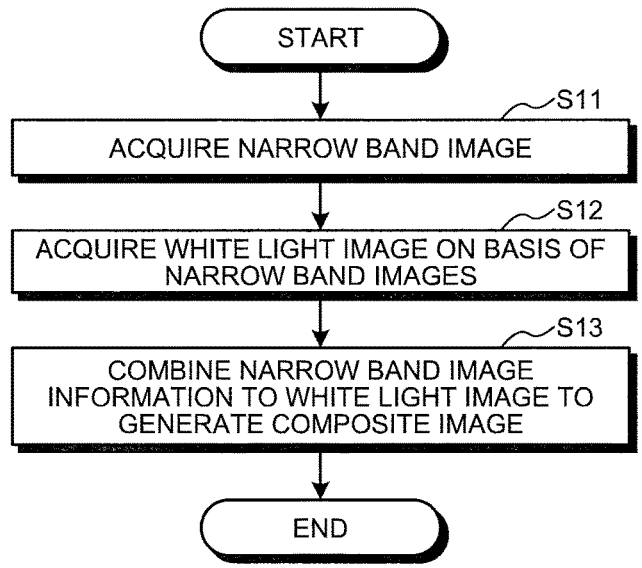
FIG. 4 is a flowchart illustrating the outline of a process performed by the image processing apparatus according to the second embodiment of the present disclosure.

FIG. 4 is a flowchart illustrating the outline of a process performed by the image processing apparatus 4. First, a narrowband image acquisition unit 41 acquires a narrowband image (step S11). The narrowband image acquisition unit 41 acquires for example the five narrowband images ([415] image, [460] image, [540] image, [600] image, [630] image) described above.

Next, the white light image acquisition unit 52 acquires a white light image on the basis of narrowband images (step S12). Specifically, the narrowband image composition unit 521 combines narrowband images corresponding to the R, G, and B bands to acquire an image corresponding to the white light image.

Figure 5:
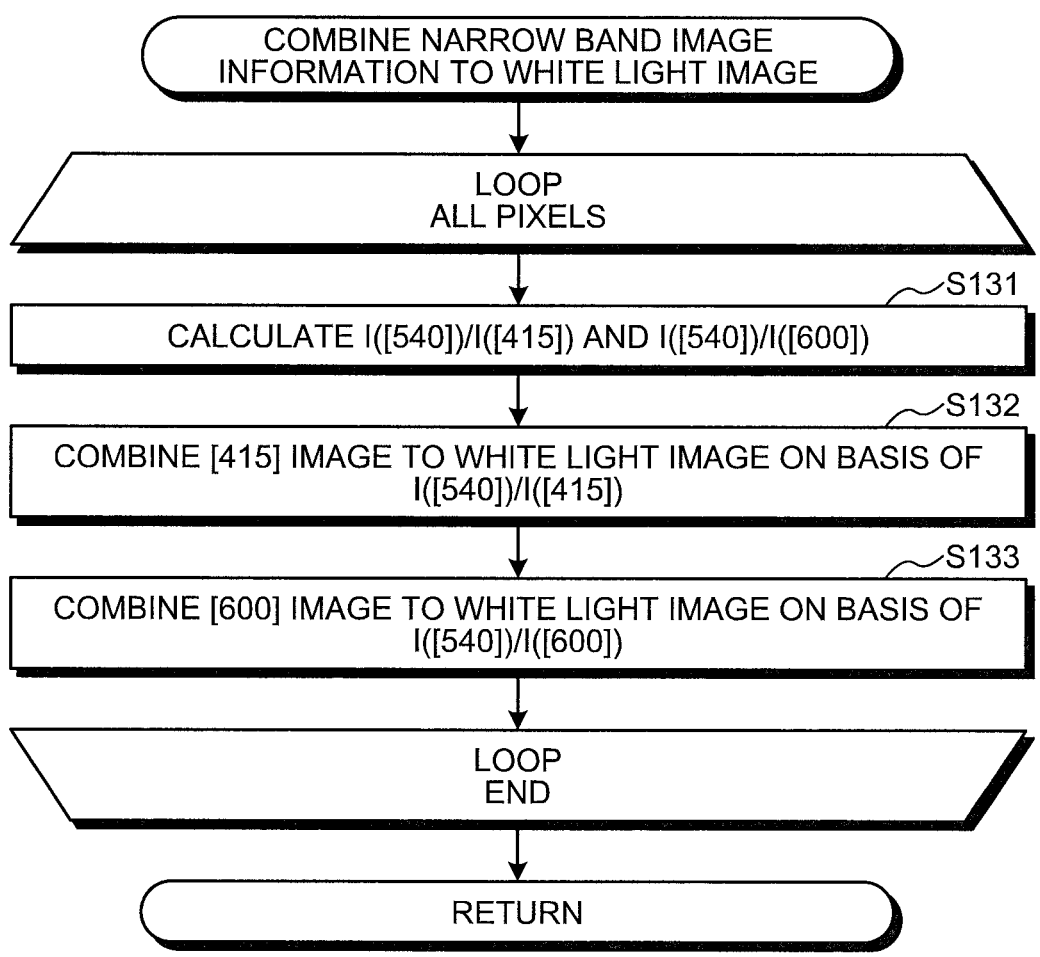
FIG. 5 is a flowchart illustrating the outline of a process performed by a composite image generation unit of the image processing apparatus according to the second embodiment of the present disclosure.

Then, the composite image generation unit 53 combines narrowband image information to the white light image to generate a composite image for display (step S13). FIG. 5 is a flowchart illustrating the outline of a process performed by the composite image generation unit 53. The process performed by the composite image generation unit 53 will be described below with reference to FIG. 5.

The composite image generation unit 53 performs the process of steps S131 to S133 described below, for all pixels. First, in step S131, the depth-correlated feature calculation unit 531 calculates the ratio "I([540])/I([415])" between intensities in the [415] image and the [540] image, and the ratio "I([540])/I([600])" between intensities in the [540] image and the [600] image (step S131).

Next, the composite image generation unit 53 combines the [415] image to the white light image, on the basis of the ratio "I([540])/I([415])" (step S132). Specifically, the composite image generation unit 53 calculates a B component according to formula (4).

Then, the composite image generation unit 53 combines the [600] image to the white light image, on the basis of the ratio "I([540])/I([600])" (step S133). Specifically, the composite image generation unit 53 calculates an R component according to formula (5). Note that the composite image generation unit 53 may perform step S132 and step S133 in reverse order or in parallel.

After the composite image generation unit 53 terminates the process for all pixels, the image processing apparatus 1 terminates a series of process steps.

According to the second embodiment of the present disclosure described above, as in the first embodiment, the narrowband image information may be combined to the white light image, according to the depth of a submucosal object, to generate the composite image for display, so that an image having the characteristics of the white light image and the narrowband image may be generated, and the narrowband image information may be applied without changing the original view of a structure showed in the white light image.

Furthermore, according to the present second embodiment, the combining of the narrowband image and the white light image is controlled on the basis of the feature correlated to the depth, and thus the change in view of the structure showed in the white light image may be prevented, and an image more suitable for observation may be provided.

Note that, in the present second embodiment, combining the narrowband image for generation of the white light image is described, but for example, the [630] image, the [540] image, and the [460] image may be respectively defined as the R component, the G component, and the B component of the white light image.

Furthermore, in the present second embodiment, combining of the intensity as the narrowband image information is described, but the information to be combined is not limited to the intensity, and, for example, a frequency component may be employed. Furthermore, the narrowband image is not limited to these two kinds of images, and, for example, only information about the [415] image may be employed.

Furthermore, in the present second embodiment, for example, light of two narrowbands included in a wavelength band corresponding to any one of the R, G, B may be also used. In this case, a weight common to the light of two narrowbands may be used.

ADVANTAGEOUS EFFECTS OF DISCLOSURE

According to the present disclosure, the narrowband image information may be combined to the white light image, according to a depth of a submucosal object, to generate a composite image for display, so that an image having the characteristics of the white light image and the narrowband images may be generated, and the narrowband image information may be applied without changing the original view of a structure showed in the white light image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
one or more processors comprising hardware, wherein the one or more processors are configured to:
acquire a narrowband image showing inside of a lumen, wherein the narrowband image is captured based on light of a predetermined wavelength band;
acquire a white light image showing the inside of the lumen; and
combine information of the narrowband image to the white light image to generate a composite image for display,
wherein in combining the information of the narrowband image to the white light image:
for the narrowband image captured based on light of the predetermined wavelength band corresponding to a blue component of visible light, the information of the narrowband image is weighted by a weight that becomes larger as a depth of a submucosal object in the lumen to be observed becomes shallower; and
for the narrowband image captured based on light of the predetermined wavelength band corresponding to a red component of visible light, the information of the narrowband image is weighted by a weight that becomes larger as the depth of the submucosal object in the lumen to be observed becomes deeper.

2. The image processing apparatus according to claim 1, wherein the one or more processors are configured to calculate a feature correlated to the depth.

3. The image processing apparatus according to claim 2, wherein the feature is a relative intensity between the narrowband images.

4. The image processing apparatus according to claim 1, wherein the submucosal object is a blood vessel.

5. The image processing apparatus according to claim 1, wherein the one or more processors are configured to combine narrowband images of wavelength bands corresponding to a red component, a green component, and a blue component of visible light to acquire an image corresponding to the white light image.

6. An image processing method comprising:
acquiring a narrowband image showing inside of a lumen, wherein the narrowband image is captured based on light of a predetermined wavelength band;
acquiring a white light image showing the inside of the lumen; and
combining information of the narrowband image to the white light image to generate a composite image for display,
wherein in combining the information of the narrowband image to the white light image:
for the narrowband image captured based on light of the predetermined wavelength band corresponding to a blue component of visible light, the information of the narrowband image is weighted by a weight that becomes larger as a depth of a submucosal object in the lumen to be observed becomes shallower; and
for the narrowband image captured based on light of the predetermined wavelength band corresponding to a red component of visible light, the information of the narrowband image is weighted by a weight that becomes larger as the depth of the submucosal object in the lumen to be observed becomes deeper.

7. A non-transitory computer-readable recording medium containing an executable program, the executable program instructing one or more computers to execute:
acquiring a narrowband image showing inside of a lumen, wherein the narrowband image is captured based on light of a predetermined wavelength band;
acquiring a white light image showing the inside of the lumen; and combining information of the narrowband image to the white light image to generate a composite image for display,
wherein in combining the information of the narrowband image to the white light image:
  for the narrowband image captured based on light of the predetermined wavelength band corresponding to a blue component of visible light, the information of the narrowband image is weighted by a weight that becomes larger as a depth of a submucosal object in the lumen to be observed becomes shallower; and
  for the narrowband image captured based on light of the predetermined wavelength band corresponding to a red component of visible light, the information of the narrowband image is weighted by a weight that becomes larger as the depth of the submucosal object in the lumen to be observed becomes deeper.

* * * * *